(12) United States Patent
Pauly et al.

(10) Patent No.: US 6,406,720 B1
(45) Date of Patent: *Jun. 18, 2002

(54) COSMETIC CONTAINING PLANT EXTRACTS

(75) Inventors: Gilles Pauly, Nancy; Marie Fleury, Paris, both of (FR)

(73) Assignee: Laboratoires Serobiologiques (Societe Anonyme), Pulnoy (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/455,402

(22) Filed: Dec. 6, 1999

Related U.S. Application Data

(63) Continuation-in-part of application No. PCT/FR98/01159, filed on Jun. 5, 1998.

(30) Foreign Application Priority Data

Jun. 6, 1997 (FR) .............................. 97 07207

(51) Int. Cl.$^7$ .......................... A61K 7/00; A61K 35/78
(52) U.S. Cl. ........................ 424/725; 424/401
(58) Field of Search .................. 424/195.1, 725, 424/401

(56) References Cited

PUBLICATIONS

Barrett, Econ, Bot., 48 (1), p. 8–20, 1994.*
Miyashiro et al., Int. Conf. AIDS, vol. 10, No. 2, p. 112, 1994.*
Watt et al., "The Medicinal and Poisonous Plants of Southern and Eastern Africa", E & S Livingstone LTD., Edinburgh and London, p. 1017, 1962.*
Sawhney et al., Pak. J. Sci. Ind. Res., 21, 193–96, 1978.*
Chhabra et al., J. Ethnopharmacol., 39(2), p. 83–103, 1994.*
Konishi et al., "Testosterone–5.alpha. –Reductase Inhibitor is Extd. from Medicinal Plants", *Chemical Abstracts*, Abstract No. XP–002052904.
Siang, "Use of combined Traditional Chinese and Western Medicine in the Management of Burns", *Chemical Abstracts*, Abstract No. XP–002052905.
Ajao et al., "Antibacterial Effect of Aqueous and Alcohol Extracts of Spondias mombin, and Alchornea Cordifolia", *Chemical Abstracts*, Abstract No. XP–002052906.
McLean et al., "Unambiguous Structural and Nuclear Magnetic Resonance Spectral Characterization of Two Triterpenoids of Maprouna Quaianensis by Two–Dimensional Nuclear Magnetic Resonance Spectroscopy", *Chemical Abstracts*, Abstract No. XP–002052907.

* cited by examiner

*Primary Examiner*—David M. Naff
*Assistant Examiner*—Mike Meller
(74) *Attorney, Agent, or Firm*—Young & Thompson

(57) ABSTRACT

A cosmetic composition containing plant extracts is disclosed. The composition has anti-free radical action, anti-aging and stimulates reduced glutathione auto-synthesis. The plant extracts are solvent extracts from *Spondias mombin, Maprounea guianesis, Waltheria indica, Gouania blanchetiana, Cordia schmoburgkii, Randia armata* and *Hibiscus furcellatus.*

11 Claims, No Drawings

COSMETIC CONTAINING PLANT EXTRACTS

This application is a continuation-in-part of International Application PCT/FR98/01159 filed on Jun. 5, 1998, which designated the United States of America.

The invention concerns the cosmetics, more particularly the dermo-cosmetics field, and its subject is the use of plant extracts, found especially in Haut-Maroni (French Guiana), in the preparation of cosmetics for the skin, mucous membrane and/or exoskeleton (hair, nails, . . . ).

The Aluku women (Haut-Maroni, French Guiana) traditionally carry out their ritual intimate ablutions every morning and evening with a plant decoction specific to each stage of a woman's life, using a large number of local plants.

The plants are prepared by decoction then used in a hip bath according to the stage in the menstrual cycle and the required effect.

A study of these various plants has revealed some specific pharmaceutical properties, namely antiseptic, healing, astringent and tonic properties (see "Végétaux utilisés pour l'hygiène intime des femmes Aluku en Guyane Française: interprétation culturelle et intérêt pharmacologique" (Plants used for intimate hygiene of Aluku women in French Guiana: cultural interpretation and pharmacological importance), Marie FLEURY, Proceedings of the $2^{nd}$ European Colloquium on Ethno-pharmacology and the $11^{th}$ international Conference on Ethno-medicine, Heidelberg, Mar. 24–27, 1993).

The inventors of this invention have made the unexpected and surprising discovery that extracts of some of the above-mentioned plants have not only the fore-mentioned pharmacological properties but also clear anti-free-radical, anti-ageing and glutathione auto-synthesis reducing properties and action, which are at least equivalent—if not superior—to those of the active Ingredients normally used in cosmetics.

The main subject of the invention is thus the use, as an active ingredient for the preparation of a cosmetic for topical use on the skin, mucous membrane and/or exoskeleton, of at least one extract or mixture of extracts from a plant selected from the group made up of *Spondias mombin, Maprounea guianensis, Waltheria indica, Gouania blanchetiana, Cordia schomburgkii, Randia armata* and *Hibiscus furcellatus,* particularly with an enhanced anti-radical and glutathione auto-synthesis reducing action.

This action may in particular be advantageously used in anti-ageing, anti-physical-stress (UV-R), cold, heat, wind and anti-chemical stress (especially pollution) and light-protective cosmetics, in anti-stress and light-protective capillary preparations or in sun or after-sun products.

The above-mentioned extracts may for example be prepared from the whole plant or plants.

However the plant extracts are advantageously obtained from the aerial parts of the plant, for example the stems, leaves, flowers and/or buds.

Once collected the plants or parts of the plants in question, posssibly after being dried, are subjected to an extraction process, preferably in two successive operations producing two different extracts. The extracting solvent used may advantageously be chosen from the group formed by water, aqueous solutions with different pH levels, C1–C6 alcohols, ketones (acetone, methylketone, diethylketone), halogenated hydrocarbons, esters (ethyl acetate, propyl actetate, butyl acetate or the like), polyhydric alcohols (glycols, diethylene glycol, Propane diol, dipropylene glycol, butylene glycol) or mixtures of at least two of the fore-mentioned substances.

In a special embodiment of the invention the plant extract(s) comprise one or more separated, purified fractions extracted from one or more of the plants.

To obtain a cosmetic composition which also has an enhanced anti-elastase action, protecting and repairing the elastic fibres of the dermis better than the anti-ageing active ingredients currently used in cosmetics, the active ingredient incorporated in it is advantageously at least one plant extract selected from the group formed by *Spondias mombin, Maprounea guianensis, Gouania blanchetiana, Waltheria indica* and *Cordia schomburgkii.*

To obtain a cosmetic composition which also has a strong anti-collagenase action, the active ingredient incorporated in it is advantageously at least one plant extract chosen from the group formed by of *Spondias mombin, Maprounea guianensis, Waltheria indica* and *Randia armata.*

To obtain a cosmetic composition which also has a strong anti-UVA effect, the active ingredient incorporated in it is advantageously at least one plant extract chosen from the group formed by *Spondias mombin, Maprounea guianensis* and *Waltheria indica.*

To obtain a cosmetic composition which additionally has a strong anti-UVB effect, the active ingredient incorporated in it is advantageously at least one plant extract chosen from the group formed by *Spondias mombin, Maprounea guianensis, Waltheria indica, Gouania blanchetiana* and *Randia armata.*

To obtain a cosmetic composition which additionally has an enhanced anti-tyrosinase action, inducing a better de-pigmenting effect than current de-pigmenting ingredients, the active ingredient incorporated in it is advantageously at least one plant extract chosen from the group formed by *Spondias mombin, Maprounea guianensis* and *Gouania blanchetiana.*

To obtain a cosmetic composition which also has a strong cellular metabolism stimulating action, the active ingredient incorporated in it is advantageously at least one plant extract chosen from the group formed by *Spondias mombin, Maprounea guianensis, Gouania blanchetiana, Cordia schomburgkii* and *Hibiscus furcellatus.*

To obtain a cosmetic composition which also has an enhanced anti-glycosylation action, the active ingredient incorporated in it is advantageously at least one plant extract chosen from the group formed by *Spondias mombin, Maprounea guianensis, Gouania blanchetiana* and *Cordia schomburgkii.*

In a preferred embodiment of the invention producing an active ingredient which simultaneously has a good anti-tyrosinase action, a very strong anti-protease action (anti-elastase and anti-collagenase), a very strong anti-UVA and anti-UVB action, a significant cellular metabolism stimulating action and a significant anti-glycosylation affect, it may be envisaged that the active ingredient will preferably be an extract or a mixture of extracts obtained from the *Spondias mombin* plant and/or the *Maprounea guianensis* plant.

As a non-restrictive illustration, various methods which are preferably used to make the above-mentioned plant extracts will now be described:

Thus a method of preparing an aqueous extract may for example comprise the following stages:

suspending the ground plant material in 5 to 10 volumes of distilled water in a reactor;

extracting for one hour at 85–90° C. with agitation;

cooling to room temperature;

centrifuging for 15 min at 5000 g or coarse filtering;

clarifying if necessary on deep filters, up to 0.5 μm;

noting the volume of extract E1 collected and determining its content of dry material;

extracting and treating the moist residue under the same conditions to obtain an extract E2;

dehydrating the two extracts by spraying the plant extract, possibly after including an additive such as maltodextrin (2/3 additive to 1/3 extracted material). [Inlet temperature: 185–190° C./outlet temperature: 75–80° C.]

A method of preparing an aqueous alcohol extract may for example comprise the following stages:

suspending the ground plant material in 5 to 10 volumes of aqueous ethanol in a reactor;

extracting with agitation for one hour under reflux;

filtering through a Buchner funnel fitted with a deep filter;

collecting the supernatant material, evaporating the ethanol phase at reduced pressure, centrifuging if necessary for 10 min at 5000 g to eliminate insoluble material, and filtering;

extracting and treating the moist residue under the same conditions to obtain an extract E2;

dehydrating the two extracts by direct spraying of the plant extract, possibly after including an additive such as maltodextrin (2/3 additive to 1/3 extracted material).

A method of preparing an alcohol extract may for example comprise the following stages:

suspending the ground plant material in 5 to 10 volumes of ethanol in a reactor;

extracting with agitation for one hour under reflux;

cooling to room temperature;

filtering through a Buchner funnel fitted with a deep filter;

evaporating the alcohol at reduced pressure at 45° C.;

drying in an oven at 40° C.;

extracting and treating the moist residue under the same conditions to obtain an extract E2.

By carrying out the preparation processes described above various extracts have been obtained from the plants in question, as mentioned in Examples 1 to 7 below.

EXAMPLE 1

Dry leaves of *Spondias mombin* were treated by the operating methods previously described, to obtain aqueous, alcoholic and aqueous alcohol extracts.

The following results were obtained:

| Extract (properties) | Aqueous | Aqueous alcohol (50% ethanol) | Ethanol |
|---|---|---|---|
| Weight of material treated (g) | 200 | 200 | 200 |
| First extract E1 | | | |
| Colour | dark brown | brown | green |
| Extraction yield (%) | 17.12 | 23.00 | |
| Dry weight of extract after drying (g) | 26.02 | 33.90 | 37.35 |
| True yield after drying (%) | 13.01 | 16.95 | 18.68 |

-continued

| Extract (properties) | Aqueous | Aqueous alcohol (50% ethanol) | Ethanol |
|---|---|---|---|
| Second extract E2 | | | |
| Colour | brown | brown | dark brown |
| Extraction yield (%) | 7.29 | 7.60 | |
| Dry weight of extract after drying (g) | 8.14 | 9.23 | 9.38 |
| True yield after drying (%) | 4.07 | 4.62 | 4.69 |
| Total yield (%) | 17.08 | 21.57 | 23.37 |

It will be noted that the extraction yield corresponds to the extracted material present in the solution, that is to say (volume of extract×content of dry material)×100 weight of starting material and that the true yield after drying corresponds to the yield of material obtained in dry form and allows for losses during the drying process.

EXAMPLE 2

Dry leaves of *Maprounea guianensis* were treated by the operating methods previously described.

The following results were obtained:

| Extract (properties) | Aqueous | Aqueous alcohol (50% ethanol) | Ethanol |
|---|---|---|---|
| Weight of material treated (g) | 200 | 200 | 200 |
| First extract E1 | | | |
| Colour | orange-brown | brown | brown |
| Extraction yield (%) | 6.87 | nd | |
| Dry weight of extract after drying (g) | 7.00 | 36.65 | 24.67 |
| True yield after drying (%) | 3.50 | 18.33 | 12.34 |
| Second extract E2 | | | |
| Colour | orange-brown | brown | dark brown |
| Extraction yield (%) | 13.25 | nd | |
| Dry weight of extract after drying (g) | 15.04 | 25.14 | 13.30 |
| True yield after drying (%) | 7.52 | 12.57 | 6.65 |
| Total yield (%) | 11.02 | 30.90 | 18.99 |

EXAMPLE 3

Dry leaves of *Gouania blanchetiana* were treated by the operating methods previously described.

The following results were obtained:

| Extract (properties) | Aqueous | Aqueous alcohol (50% ethanol) | Ethanol |
|---|---|---|---|
| Weight of material treated (g) | 200 | 200 | 200 |
| First extract E1 | | | |
| Colour | brown | brown | green |
| Extraction yield (%) | 6.10 | 11.86 | |
| Dry weight of extract after drying (g) | 8.90 | 13.28 | 13.87 |
| True yield after drying (%) | 4.45 | 6.64 | 6.94 |
| Second extract E2 | | | |
| Colour | brown | brown | dark brown |
| Extraction yield (%) | 5.05 | 5.00 | |
| Dry weight of extract after drying (g) | 5.07 | 4.67 | 5.22 |
| True yield after drying (%) | 2.54 | 2.34 | 2.61 |
| Total yield (%) | 6.99 | 8.98 | 9.55 |

EXAMPLE 4

Dry leaves of *Cordia schomburgkii* were treated by the operating methods previously described to obtain alcoholic and aqueous alcohol extracts.

In this example extracts E1 and E2 of the alcoholic extract were combined before drying: (for aqueous alcohol extraction an additive is included before spraying: the corresponding weights are the weights of dry material not counting the weight of additive).

The following results were obtained:

| Extract (properties) | Aqueous alcohol (70% ethanol) | Ethanol |
|---|---|---|
| Weight of material treated (g) | 200 | 200 |
| First extract E1 | | |
| Colour | green | green |
| Extraction yield (%) | 14.60 | |
| Dry weight of extract after drying (g) | 20.81 | 17.16 |
| True yield after drying (%) | 10.41 | 8.58 |
| Second extract E2 | | |
| Colour | | green |
| Extraction yield (%) | | |
| Dry weight of extract after drying (g) | | 10.13 |
| True yield after drying (%) | | 5.07 |
| Total yield (%) | | 13.65 |

EXAMPLE 5

A mixture of leaves and dry buds of *Waltheria indica* was treated by the operating methods previously described to obtain aqueous, alcoholic and aqueous alcohol extracts.

The following results were obtained:

| Extract (properties) | Aqueous | Aqueous alcohol (50% ethanol) | Ethanol |
|---|---|---|---|
| Weight of material treated (g) | 150 | 150 | 150 |
| First extract E1 | | | |
| Colour | brown | brown | green |
| Extraction yield (%) | 9.83 | 9.82 | |
| Dry weight of extract after drying (g) | 7.27 | 7.05 | 10.31 |
| True yield after drying (%) | 4.85 | 4.70 | 6.87 |
| Second extract E2 | | | |
| Colour | brown | brown | green |
| Extraction yield (%) | 5.05 | 1.70 | |
| Dry weight of extract after drying (g) | 4.03 | 2.16 | 3.06 |
| True yield after drying (%) | 2.69 | 1.44 | 2.04 |
| Total yield (%) | 7.53 | 6.14 | 8.91 |

EXAMPLE 6

Dry leaves of *Randia armata* were treated by the operating methods previously described to obtain aqueous, alcoholic and aqueous alcohol extracts.

In this example extracts E1 and E2 were combined before drying: (for aqueous and aqueous alcohol extraction an additive is included before spraying: the corresponding weights are the weights of extracted material not counting the weight of additive).

The following results were obtained:

| Extract (properties) | Aqueous | Aqueous alcohol (50% ethanol) | Ethanol |
|---|---|---|---|
| Weight of material treated (g) | 200 | 200 | 200 |
| First extract E1 | | | |
| Colour | light brown | brown | green |
| Extraction yield (%) | 25.50 | 36.50 | |
| Dry weight of extract after drying (g) | 34.00 | 59.75 | 51.38 |
| True yield after drying (%) | 17.00 | 29.88 | 25.69 |
| Second extract E2 | | | |
| Colour | | | green |
| Extraction yield (%) | | | |
| Dry weight of extract after drying (g) | | | 15.15 |
| True yield after drying (%) | | | 7.58 |
| Total yield (%) | | | 33.27 |

EXAMPLE

Dry leaf-bearing stems of *Hibiscus furcellatus* were treated by the operating methods previously described to obtain alcoholic and aqueous alcohol extracts.

In this example extracts E1 and E2 of the aqueous alcohol extract were combined before drying: (for aqueous alcohol extraction an additive is included before spraying: the corresponding weights are the weights of extracted material not counting the weight of additive).

The following results were obtained:

| Extract (properties) | Aqueous alcohol (50% ethanol) | Ethanol |
|---|---|---|
| Weight of material treated (g) | 150 | 150 |
| First extract E1 | | |
| Colour | brownish green | green |
| Extraction yield (%) | 8.99 | |
| Dry weight of extract after drying (g) | 7.96 | 3.78 |
| True yield after drying (%) | 5.31 | 2.52 |
| Second extract E2 | | |
| Colour | | dark brown |
| Extraction yield (%) | | |
| Dry weight of extract after drying (g) | | 1.22 |
| True yield after drying (%) | | 0.81 |
| Total yield (%) | | 3.33 |

The cosmetically important properties and action of the above-mentioned plant extracts, discovered by the inventors, have been demonstrated and quantitatively evaluated by means of various tests known in the art, which are briefly explained below and the results of which are set out in Table I.

1) Evidence of a De-pigmenting Action

To determine the de-pigmenting power of the extracts, their tyrosinase action was evaluated by measuring the product of oxidising L-DOPA to DOPACHROME (by HS Mason's method, 1948), carrying out the following stages:

mixing tyrosinase with L-DOPA in the phosphate buffer with an automatic pipette recording the optical density at 475 nm for 2 minutes, then calculating the initial speed of the enzyme reaction and determining the CI50 (concentration which halves the initial speed of DOPACROME formation).

Referring to Table I above, it will be noted that the results surprisingly and unexpectedly show a clear anti-tyrosinase effect of the plant extracts, comparable or even superior to that of the reference substance (hydroquinone).

2) Evidence of an Anti-radical Action

Aggressive action by free radicals is one of the main skin-damaging mechanisms owing to the action of stress factors in the external environment.

Free radicals, particularly the reactive forms of oxygen (superoxide radical $O_2^{\bullet}$, hydroxyl radical HO•, singlet oxygen $O_2^1$, hydrogen peroxide $H_2O_2$), act on a cellular scale: particularly damaging the membranous lipids with the formation of lipoperoxides, deterioration of proteins, blocking of enzyme systems and deterioration of the nuclear genetic capital. Noxious effects are also produced in the macromolecules of the extra-cellular matrix of the dermis, namely in collagen, elastin and glycoaminoglycans.

An equally surprising and unexpected observation was the powerful anti-radical action of the various extracts obtained (see Table I below).

This action was evaluated by the following chemical and biochemical tests in tubo:

a) Anti-free-radical action: DPPH test (C Deby, 1970)

DPPH (diphenylpicrylhydrazyl) is a stable radical which forms a violet-coloured solution when dissolved in a methanol.

A substance with an anti-radical action stabilises DPPH to a leuco-derivative (colourless).

b) Anti-HO• action: salicylic acid method (M Tien, 1992)

Iron complexed by ethylene diaminetetracetci acid forms hydroxyl radicals HO• in aqueous solution in contact with $H_2O_2$.

The hydroxyl radicals react with salicylic acid (S.A.) to form a reddish-coloured compound.

A substance with an anti-radical action absorbs the HO• radicals, thus reducing the formation of red-coloured compound.

c) Anti-HO• action: deoxyribose method (Halliwell's method, 1987 or Aruoma's method, 1988).

The hydroxyl radicals HO• are produced by Fenton's reaction:

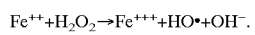

$$Fe^{++}+H_2O_2 \rightarrow Fe^{+++}+HO\bullet+OH^-.$$

The iron is complexed with EDTA in Halliwell's method and not complexed in Aruoma's method in order to evaluate the capacity for capture by the substance being evaluated (for example desferrioxamine inactivates Fenton's reaction by capturing iron).

The hydroxyl radicals are revealed by a sugar, deoxyribose (present in ADN); when HO• is present this forms a compound which reacts with thiobarbituric acid (TBA) in the form of a pink fluorescent condensate.

d) Anti-$O_2^{\bullet}$ action: luminol method (GM Oyamburo, 1970)

An enzyme system (hypoxanthine/xanthine oxidase:XOD) forms radical superoxide anions $O_2^{\bullet}$ which react with luminol to form an intermediate compound; when this compound stabilises it has a luminescence which is recorded with a photoelectron multiplier.

A substance with an anti-radical action absorbs or destroys the $O_2^{\bullet}$ anion and thus reduces the formation of luminescence.

e) Anti-$O_2$ and $H_2O_2$ action: luminol+microperoxidase method (M Israel, 1985)

An enzyme system (hypoxanthine/xanthine oxidase:XOD; forms radical superoxide anions $O_2^{\bullet}$ which gradually dismute to $H_2O_2$ and $O_2$. $H_2O_2$ and $O_2^{\bullet}$ react with microperoxidase (M) to form $O_2^1$ (singlet oxygen) which degrades luminol (Lu) to form a luminescent composition, the light emission from which is recorded with a photoelectron multiplier.

An anti-radical substance absorbs either $H_2O_2$ or $O_2^{\bullet}$ or $O_2^1$ and thus reduces the formation of luminescence.

f) Anti-$O_2^{\bullet}$ action: blue neotetrazolium (NBT) method (N Ohkuma, 1987)

An enzyme system (hypoxanthine/xanthine oxidase) forms radical superoxide anions $O_2^{\bullet}$.

The $O_2^{\bullet}$ anions react with NBT to form a red compound, formazan. An anti-radical substance absorbs or destroys the $O_2^{\bullet}$ anion and thus reduces the formation of formazan.

3) Evidence of an Anti-UV-A Action

UV-A radiation is a factor which determines ageing of the skin, either through deterioration of the dermic matrix or through cellular damage.

The surprising and unexpected observation has been made that the various plant extracts obtained are clearly active in protecting cells from UV-A.

Human fibroblasts of the MRC5 type were cultivated in a growth medium, until the tapetum cellulosum was saturated. The growth medium was then replaced with a standard medium (DMEM+SVF, 1%) containing each extract in the various quantities to be tested (see Table I).

After incubating for 48 hours at 37° C. the various media were replaced with a saline solution (Hanks), When the MRC5 were irradiated on top with fluorescent tubes.

As soon as the irradiation was over the saline solution was removed to measure the malonal dialdehyde (MDA) by reaction with warm thiobarbituric acid (fluorescence at 560 nm). MDA is a degradation product of the unsaturated lipids which make up biological membranes. It causes bridges which inhibit enzymes and form lipofuscins (ageing marks), and would be mutagenic. The MRC5 cells were recovered in dilute sodium hydroxide to measure the proteins (Bradford method) and glutathione (GSH) by means of a fluorescent probe (Hissin, 1976). GSH gives cytoplasm a reducing potential which is necessary for correct operation of the cellular mechanism; GSH also captures the reactive forms of oxygen and enables peroxide lipids to be regenerated by GSH peroxidase.

4) Evidence of the Anti-UVB Cell-protecting Effect on Human Keratinocytes Surviving in vitro UVB rays cause inflammation (erythema, oedema) by activating an enzyme, phospholipase A2.

This enzyme releases arachidonic acid from the phospholipids of the plasma membrane: arachidonic acid is the precursor of prostaglandins, which are mediators of inflammation, and E2 prostaglandins (=PGE2) are thus formed by cyclooxygenase. A431 keratinocytes are seeded in a defined medium with foetal calf serum.

After 72 hours at 37° C. with $CO_2$=5% the culture medium is replaced by a saline solution containing the plant extract to be tested.

The keratinocytes are immediately irradiated with a dose of UVB (30 $mJ/cm^2$; tubes of the DUKE FL40E type), incubated for 24 hours at 37° C., then the content of PGE2 and of LDH in the supernatant medium is measured.

The number of adhering keratinocyes is determined (after trypsination) by a particle counter and the content of PGE2 is determined by an ELISA test.

The content of LDH (lactate-dehydrogenase/cytoplasmic enzyme), which is a marker of cellular strain, is also determined by an enzyme reaction.

The action of the plant extract tested is expressed as a % variation of the two markers relative to the values obtained with the control substances (average of 2 tests, each in duplicate—see Table I).

5) Evidence of an Anti-ageing Action

Elastin is a dermic macromolecule organised as a structured network, which gives the skin its elastic properties.

The elastic network is degraded with age, with more serious damage to the uncovered parts exposed to solar radiation, and the result is loss of elasticity and great flaccidity of the skin.

One of the mechanisms of this process is enzyme hyperactivity in the digestion of elastic fibres by endogenous elastases, and the beneficial effect of elastase inhibitors as an active anti-ageing substance is well known.

The surprising and unexpected observation has been made that the extracts obtained have a clear anti-elastase action (cf. Table I).

The method used to demonstrate the inhibition of elastase is the method with synthetic substrate, chiefly comprising the following stages:

use of 1 mM N-succinyl-(Ala.; 3-para-Nitroanilide in a TRIS buffer (pH=8);

incubation of the substance with elastase and the substrate for 20 minutes at 20° C.;

appearance of yellow colouring, which is measured by spectrophotometry at 410 nm.

6) Evidence of an Anti-collagenase Action in Tubo (Van Wart's Method, 1981)

Proteases secreted by polymorphonuclear neutrophilic leukocytes when there is inflammation or by fibroblasts subjected to irradiation by UVA cause degradation of the proteins which structure the extracellular matrix of the dermis.

The anti-collagenase in tubo action of an extract is measured with a collagenase of clostridium hystoliticium and a synthetic chromogenic substrate, FALGPA.

Incubation is carried out for 30 mn at room temperature and the optical density is measured at 324 nm.

The results are expressed as % inhibition of the enzyme relative to the control substance without active ingredient (Table I).

7) Evidence of Action Inhibiting Non-enzymatic Glycation in Tubo (Devi's "Anti-glycation" Action, 1990 and Monnier's, 1984)

Non-enzymatic glycation of proteins is a process which determines the ageing of human tissues; It explains the cross-linking of extra-cellular matrices and basal membranes which is largely responsible for the pathology observed in diabetics.

In addition, Schiff's bases catalyse the production of reactive forms of oxygen which aggravate the effects of non-enzymatic glycation.

Tests in tubo were carried out on type I collagen incubated or 21 days at 45° C. in the presence of 1% glucose, and the content of Schiff's bases is evaluated by densitometry at 350 nm and by fluorimetry at 430 nm (excitation at 350 nm). The results are expressed as % inhibition of the formation or Schiff's bases relative to the control specimens (Table I).

8) Evidence of Stimulation of Cellular Metabolism

The metabolism-stimulating action brings an increase in oxygen consumption. Active ingredients which have this property participate in improved cell regeneration and may be used successfully for treating skins which are tired, stressed or exposed to pollution and for combatting the effect of ageing. Oxygen consumption is determined by polarographic measurements on a homogenate of epithelial cells using an oxygraph of the type produced by Gilson, fitted with a so-called Clark electrode.

Oxygen consumption is recorded first under control conditions (epithelial cells in a buffer), then when the substance to be tested has been added to the medium, the final concentration of that substance being 1%.

Oxygen consumption is calculated from the polarographic curves and the effect of the product is expressed as a percentage increase in oxygen consumption relative to the control conditions (in the absence of the active ingredient to be tested).

The results correspond to the mean +/- SEM of 3 tests (Table I).

As shown in Table I below, which contains the results of the 8 tests described above, all the plant extracts obtained also have a marked anti-radical action and a marked action in stimulating reduced glutathione auto-synthesis, for use in anti-ageing cosmetics, and cosmetics to counter physical stresses (UV-R, cold, heat, wind) or chemical stresses (for example pollution).

TABLE 1

| Extract | Plant | C150 anti-tyrosinase effect in % | Anti-free-radical effect in % inhibition (0.03 or 0.1% doses) | | | | | |
|---|---|---|---|---|---|---|---|---|
| | | | DPPH test | Fenton reaction | | Tests | | |
| | | | | A.S. | Desoxyribose | Lu | Lu, M | NBT |
| Ethanolic extract example 1 | *Spondias mombin* | 0.017 | 92 | 40 | 46 | 71 | 100 | 97 | 68 |
| Aqueous extract example 2 | *Maprounea guianensis* | 0.015 | 92 | 35 | 55 | 76 | 100 | 99 | 74 |
| Ethanolic extract example 2 | *Maprounea guianensis* | 0.015 | 91 | 47 | 12 | 79 | 100 | 99 | 70 |
| 50% ethanol extract example 3 | *Gouania blanchetiana* | 0.015 | 88 | 0 | 27 | 67 | 100 | 91 | 75 |
| Aqueous extract example 5 | *Waltheria indica* | 0.08 | 88 | 16 | 8 | 47 | 100 | 96 | 62 |
| 70% ethanol extract example 4 | *Cordia scomburgkii* | 0.09 | 89 | 30 | 3 | 19 | 99 | 97 | 31 |
| Aqueous extract example 6 | *Randia armata* | 0.18 | 92 | 12 | 0 | 34 | 100 | 96 | 40 |
| 50% ethanol extract example 6 | *Randia armata* | 0.13 | 92 | 18 | 0 | 42 | 100 | 96 | 38 |
| 50% ethanol extract example 7 | *Hibiscus furcellatus* | 0.83 | 86 | 19 | 0 | 14 | 99 | 42 | 10 |
| | Hydroquinone | 0.025 | | | | | | | |

| Extract | Plant | Anti-UV-A effect on MRC 5 %/control | | Anti UV-B effect on A431 %/control | | Anti-elastase effect at 0.3% | Anti-colagenase effect at 0.3% | Anti-glycation effect % inhibition of Schiff's base formation/ | Stimulation of metabolism % increase in $O_2$ consumption |
|---|---|---|---|---|---|---|---|---|---|
| | | 0.001 to 0.006% doses | | | | Inhibition in % | Inhibition in % | 0.01 to 0.1% doses | (m +/− SEM) 1% doses |
| | | MDA | GSH | PGE2 | LDH | | | | |
| Ethanolic extract example 1 | *Spondias mombin* | 61 | 30 | −73 | −88 | 87 | 99 | 43 | 93 +/− |
| Aqueous extract example 2 | *Maprounea guianensis* | 34 | 38 | −99 | −100 | 80 | 8 | 100 | 63 +/− 7 |
| Ethanolic extract example 2 | *Maprounea guianensis* | 53 | 45 | −100 | −100 | 85 | 100 | | 61 +/− 20 |
| 50% ethanol extract example 3 | *Gouania blanchetiana* | 13 | 14 | −92 | −100 | 56 | 39 | 68 | 151 +/− 48 |
| Aqueous extract example 5 | *Waltheria indica* | −43 | 71 | −25 | −70 | 48 | 83 | 3 | 57 +/− 29 |
| 70% ethanol extract example 4 | *Cordia scomburgkii* | −25 | 10 | | | 37 | 17 | 54 | 79 +/− 17 |
| Aqueous extract example 6 | *Randia armata* | −15 | 37 | 20 | −70 | 16 | 97 | 11 | −54 |
| 50% ethanol extract example 6 | *Randia armata* | −11 | 43 | −70 | −89 | 17 | 99 | | −41 |
| 50% ethanol extract example 7 | *Hibiscus furcellatus* | 0 | 42 | −2 | −17 | 17 | 13 | 0 | 118 +/− 31 |
| | Hydroquinone | | | | | | | | |

The invention also concerns a composition or a cosmetic product for external topical use on the skin, mucous membrane and/or exoskeleton containing as active ingredient(s), particularly with a high-strength anti-radical action and a high-strength action in stimulating reduced glutathione autosynthesis, alone or combined with at least one other active ingredient, at least one extract from a plant chosen from the group comprising *Spondias mombin, Maprounea guianensis, Waltheria indica, Gouania blanchetiana, Cordia schomburgkii, Randia armata* and *Hibiscus furcellatus*.

In a first preferred embodiment of the invention and with a view to obtaining a cosmetic composition which concurrently has a strong anti-tyrosinase action, anti-elastase action, anti-UVB action and anti-glycation action in addition to the advantageous properties mentioned above, the active ingredient is at least one plant extract chosen from the group formed by *Spondias mombin, Maprounea guianensis* and *Gouania blanchetiana*.

In a second preferred embodiment of the invention and with a view to obtaining a cosmetic composition which concurrently has a high-strength anti-protease (anti-elastase and anti-collagenase) action and strong anti-UVA and anti-UVB effects in addition to the advantageous properties mentioned above, the active ingredient is at least one plant extract chosen from the group formed by *Spondias mombin, Maprounea guianensis* and *Waltheria indica*.

The cosmetic composition advantageously contains as an active ingredient, alone or combined with other active ingredients, between 0.001 and 20% by weight, preferably between 0.1 and 3% by weight, of a plant extract or mixture of plant extracts as defined above.

As non-restrictive examples of embodiments of the invention various cosmetic products or preparations containing a plant extract or mixture of plant extracts as previously described will now be described.

EXAMPLE 1

A cosmetic product in the form of a bleaching cream for the skin according to the invention may for example have a composition by weight as indicated below, made up of the following fractions A, B and C.

| Fraction A: | |
| --- | --- |
| Glycerol stearate (and) Cétéareth 20 | 15% |
| Paraffin oil | 3.00% |
| Ascorbyl palmitate | 3.00% |
| Dimethicone | 3.00% |
| Cetyl alcohol | 0.50% |
| PEG 30 - glycerol isostearate | 2.00% |
| Fraction B: | |
| Water | 72.20% |
| Methylparaben | 0.20% |
| Imidazolidinyl urea | 0.30% |
| Ethanol extract of *Gouania blanchetiana* (as in Example 3) | 0.50% |
| Fraction C: | |
| Perfume | 0.30% |

The method of preparing and producing the above-mentioned cream comprises melting the fraction A ingredients with agitation at 75° C., preparing fraction B at 75° C., then pouring fraction A into fraction B with agitation by a turbine, cooling with agitation by a planetary gear and adding fraction C.

EXAMPLE 2

A cosmetic product in the form of an anti-stain emulsion for the hands according to the invention may for example have a composition by weight as indicated below, made up of the following fractions A, B and C.

In accordance with the invention the emulsion may also be a multiple-action product particularly with an anti-radical, anti-UVA and anti-UVB, anti-protease, anti-glycation and cellular metabolism-stimulating action.

| Fraction A: | |
| --- | --- |
| Glycerol stearate (and) Stearate PEG 100 | 6.00% |
| Oleic alcohol | 1.50% |
| Glycerol stearate | 2.00% |
| 2-steareth | 2.00% |
| Shea butter | 3.00% |
| Dimethicone | 4.00% |
| Caprylic/capric triglyceride | 8.00% |
| Propylparaben | 0.10% |
| Tocopherol acetate | 0.10% |
| Fraction B: | |
| Water | 62.30% |
| Elestab 388 (Laboratoires Sérobiologiques) | 2.50% |
| Aqueous extract of *Maprounea guianensis* (as in Example 2) | 1.00% |
| Ethanol extract of *Spondias mombin* (as in Example 1) | 0.50% |
| Propylene glycol | 5.00% |

| -continued | |
| --- | --- |
| Fraction C: | |
| Polyacrylamide (and) isoparaffin (and) Laureth 7 | 2.00% |

The method of preparing and producing the above-mentioned emulsion comprises preparing fractions A and B separately at 75° C., adding fraction A to fraction B with agitation by a turbine at 75° C., then cooling the mixture obtained to 50° C. and adding fraction C, and lastly cooling the final mixture to room temperature.

EXAMPLE 3

A cosmetic product in the form of an anti-stress, light-protective conditioner for dry hair according to the invention may for example have a composition by weight as indicated below, made up of the following fractions A and B.

| Fraction A: | |
| --- | --- |
| Cetyl alcohol | 2.00% |
| Liquid paraffin | 2.00% |
| Sorbitol stearate | 1.00% |
| Isopropyl palmitate (and) castor oil | 1.00% |
| Fraction B: | |
| Glycerin | 2.00% |
| Laureth 20 | 1.00% |
| Cetrimonium chloride | 2.00% |
| Ethanol extract of *Spondias mombin* (as in Example 1) | 0.50% |
| Aqueous extract of *Randia armata* | 0.10% |
| Elestab 388 (Laboratoires Sérobiologiques) | 1.50% |
| Water sufficient to make up | 100.00% |

The method of preparing and producing the above-mentioned conditioner comprises preparing fractions A and B separately with agitation at 80° C., adding fraction A to fraction B with agitation by a turbine and finally cooling the mixture obtained to room temperature.

EXAMPLE 4

A cosmetic product in the form of an anti-stress protective body cream according to the invention may or example have a composition by weight as indicated below, made up of the following fractions A, B and C.

| Fraction A: | |
| --- | --- |
| Glycerol stearate (and) Cétéareth 20 (and) Cétéareth 10 (and) ketostearylic alcohol (and) cetyl palmitate | 6.00% |
| Ketostearylic alcohol | 1.00% |
| Decyl oleate | 3.00% |
| Liquid paraffin | 4.00% |
| Shea butter | 2.00% |
| Fraction B: | |
| Glycerin | 3.00% |
| Hydrolysed wheat proteins | 0.50% |
| Ethanol extract of *Hibiscus furcellatus* (as in Example 7)[1] | 1.25% |
| Aqueous extract of *Randia armata* (as in Example 6) | 0.60% |

| | |
|---|---|
| Ethanol extract of *Cordia schomburgkii* (as in Example 4) | 0.20% |
| Water | 78.25% |
| Fraction C: | |
| Perfume | 0.20% |

¹Translator's Note:
There are only 5 examples.

The method of preparing and producing the above-mentioned emulsion comprises preparing fractions A and B separately with agitation at 80° C., adding fraction A to fraction B with agitation by a turbine, then bringing the mixture obtained back to room temperature and adding Fraction C.

EXAMPLE 5

A cosmetic product in the form of an anti-ageing, multiple-action (anti-radical, anti-UVA and anti-elastase) day cream according to the invention may for example have a composition by weight as indicated below, made up of the following fractions A, B and C.

| | |
|---|---|
| Fraction A: | |
| Glycerol stearate | 14.00% |
| Octyl dodecanol | 6.00% |
| Dibutyl adipate | 6.00% |
| Céteareth 12 | 1.50% |
| Céteareth 20 | 1.50% |
| Fraction B: | |
| Propylene glycol | 5.00% |
| Ethanol extract of *Maprounea guianensis* (as in Example 2) | 0.75% |
| Aqueous extract of *Waltheria indica* (as in Example 5) | 1.00% |
| Ethanol extract of *Randia armata* (as in Example 6) | 0.50% |
| Elestab 4112 (Laboratoires Sérobiologiques) | 0.40% |
| Water sufficient to make up | 100.00% |
| Fraction C: | |
| Perfume | 0.20% |

The method of preparing and producing the above-mentioned cream comprises preparing fractions A and B separately with agitation at 80° C., adding fraction A to fraction B with agitation by a turbine, cooling the mixture obtained to 45° C., then adding fraction C and lastly bringing the final mixture back to room temperature.

The invention is not of course limited to the embodiments described. Modifications are still possible, particularly in respect of the constitution of the various components or substitution of equivalent techniques, without going beyond the scope of protection of the invention.

What is claimed is:

1. A method of stimulating reduced glutathione autosynthesis, comprising applying to healthy facial skin of a patient a cosmetic composition containing an effective amount of at least one solvent extract of a plant selected from the group consisting of *Spondias mombin, Maprounea guianesis, Waltheria indica, Gouania blanchetiana, Cordia schmoburgkii, Randia armata* and *Hibiscus furcellatus*.

2. Method according to claim 1, wherein said at least one extract is obtained from the aerial part of the plant.

3. Method according to claim 1, wherein the solvent is selected from the group consisting of water, aqueous solutions with different pH levels, C1–C6 alcohols, ketones, halogenated hydrocarbons, esters, polyhydric alcohols and mixtures thereof.

4. Method according to claim 1, wherein the extract is from at least one plant extract selected from the group consisting of *Spondias mombin, Maprounea guianensis, Gouania blanchetiana, Waltheria indica* and *Cordia schomburgkii*.

5. Method according to claim 1, wherein the extract is from at least one plant extract selected from the group consisting of *Spondias mombin, Maprounea guianesis, Waltheria indica* and *Randia armata*.

6. Method according to claim 1, wherein the extract is from at least one plant extract selected from the group consisting of *Spondias mombin, Maprounea guianesis* and *Waltheria indica*.

7. Method according to claim 1, wherein the extract is from at least one plant extract selected from the group consisting of *Spondias mombin, Maprounea guianesis, Waltheria indica, Gouania blanchetiana* and *Randia armata*.

8. Method according to claim 1, wherein the extract is from at least one plant extract selected from the group consisting of *Spondias mombin, Maprounea guianesis, Gouania blanchetiana* and *Waltheria indica*.

9. Method according to claim 1, wherein the extract is from at least one plant extract selected from the group consisting of *Spondias mombin, Maprounea guianesis, Gouania blanchetiana, Cordia schomburgkii* and *Hibiscus furcellatus*.

10. Method according to claim 1, wherein the extract is from at least one plant extract selected from the group consisting of *Spondias mombin, Maprounea guianensis, Gouania blanchetiana* and *Cordia schomburgkii*.

11. Method according to claim 1, wherein the extract is from at least one plant extract selected from the group consisting of *Spondias mombin* and *Maprounea guianensis*.

* * * * *